(12) United States Patent
Robertson

(10) Patent No.: US 6,936,157 B2
(45) Date of Patent: Aug. 30, 2005

(54) INTERFERENCE CORRECTION OF ADDITIVES CONCENTRATION MEASUREMENTS IN METAL ELECTROPLATING SOLUTIONS

(75) Inventor: Peter M. Robertson, Hoehenschaftlarn (DE)

(73) Assignee: Advanced Technology Materials, Inc., Danbury, CT (US)

( * ) Notice: Subject to any disclaimer, the term of this patent is extended or adjusted under 35 U.S.C. 154(b) by 531 days.

(21) Appl. No.: 10/215,586

(22) Filed: Aug. 9, 2002

(65) Prior Publication Data

US 2003/0080000 A1 May 1, 2003

Related U.S. Application Data

(60) Provisional application No. 60/311,700, filed on Aug. 10, 2001.

(51) Int. Cl.[7] .............................................. G01N 27/42
(52) U.S. Cl. ....................... 205/775; 205/81; 205/787; 204/434
(58) Field of Search ................................. 204/400, 434; 205/81, 775, 787

(56) References Cited

U.S. PATENT DOCUMENTS

| | | | |
|---|---|---|---|
| 5,192,403 A | | 3/1993 | Chang et al. |
| 5,223,118 A | * | 6/1993 | Sonnenberg et al. ........ 205/81 |
| 6,280,602 B1 | | 8/2001 | Robertson |
| 6,572,753 B2 | * | 6/2003 | Chalyt et al. ................ 205/81 |
| 6,808,611 B2 | * | 10/2004 | Sun et al. ..................... 205/81 |

FOREIGN PATENT DOCUMENTS

| | | | |
|---|---|---|---|
| DE | 19911447 A | | 12/2000 |
| WO | WO 01/29548 | * | 4/2001 |

OTHER PUBLICATIONS

Derwent Abstract of DE 19911447 A, Schmacher, et al., Dec. 7, 2000.

JPO Computer Translation of JP 2001-073183, Yasushi, et al, Mar. 21, 2001.

* cited by examiner

Primary Examiner—Kaj K. Olsen
(74) Attorney, Agent, or Firm—Margaret Chappuis; Yongzhi Yang; John Boyd (57) ABSTRACT

The present invention relates to a method and apparatus for determining concentrations of various organic additives in metal electroplating solutions, by utilizing a mathematical correction model in combination with the conventional PCGA chrono-potentiometric analysis method, to eliminate the interaction between the observed electrochemical behavior of various organic additives, and to achieve accurate concentration determination of such additives.

23 Claims, 10 Drawing Sheets

INTERFERENCE CORRECTION OF ADDITIVES CONCENTRATION MEASUREMENTS IN METAL ELECTROPLATING SOLUTIONS

This application claims the benefit of provisional application 60/311,700 filed Aug. 10, 2001.

BACKGROUND OF THE INVENTION

1. Field of Invention

The present invention relates to concentration determination of organic additives contained in a metal electroplating solution, and more specifically to a method for determining concentration of suppressor, accelerator, and/or leveler in aqueous acid metal electroplating solutions, by mathematically eliminating the cross-interference between the effects of these additives.

2. Related Art

The Pulsed Cyclic Galvanostatic Analysis (PCGA) provides a method for accurately determining the variety of organic constituents usually contained in metal electrochemical plating baths, such as suppressors, accelerators, and levelers. It is a chrono-potentiometric method wherein the plating currents are set constant, and plating over-potentials are conveniently measured and used to quantify the concentrations of various constituents in the electrochemical plating baths.

Robertson U.S. Pat. No. 6,280,602 (hereinafter "Robertson patent") discloses a PCGA-based method and apparatus for indirect determination of the concentrations of various organic additives in the metal plating baths, which is capable of determining such concentrations with a high degree of accuracy (usually less than 10 percent of error rate).

However, the Robertson patent does not take into account the interacting and interfering effects of various additives on the measured electroplating potential, which may affect the accuracy of the calculated additive concentrations based on such measured electroplating potential. For example, the increment of the leveler concentration in the metal plating bath reduces the accelerator response, leading to under-reading of the accelerator concentration, while the increment of the accelerator concentration increases the leveler response, leading to over-reading of the leveler concentration.

Therefore, it is an object of the present invention to provide a method for correcting the additive concentrations calculated, according to the conventional PCGA-based method, so as to eliminate the interaction and interference between various additives.

Other objects and advantages will be more fully apparent form the ensuing disclosure and appended claims.

SUMMARY OF THE INVENTION

One aspect of the present invention relates to a method for determining concentration(s) of a suppressor and/or an accelerator in a sample metal plating solution that contains both the suppressor and the accelerator, comprising the steps of:

(a) preparing a plurality of calibration solutions, each of which contains the suppressor and the accelerator in different, known concentrations;

(b) measuring electroplating potential that is characteristic of a calibration solution;

(c) calculating concentrations of the suppressor and the accelerator in the calibration solution, according to Pulsed Cyclic Galvanostatic Analysis of the measured electroplating potential of the calibration solution;

(d) repeating steps (b) to (c) for each calibration solution, to obtain calculated concentrations of the suppressor and the accelerator in each calibration solution;

(e) determining correction coefficients for the suppressor and/or the accelerator, based on the known concentrations of the suppressor and/or the accelerator and the calculated concentrations of the suppressor and the accelerator in the calibration solutions;

(f) measuring electroplating potential that is characteristic of the sample metal plating solution;

(g) calculating concentrations of the suppressor and the accelerator in the sample metal plating solution, according to Pulsed Cyclic Galvanostatic Analysis of the measured electroplating potential of the sample metal plating solution; and (h) determining corrected concentration(s) of the suppressor and/or the accelerator in the sample metal plating solution, based on the calculated concentrations of the suppressor and the accelerator in said sample metal plating solution and the correction coefficients determined in step (e) for the suppressor and/or the accelerator.

In a preferred embodiment, the correction coefficients for both the suppressor and the accelerator are determined, so that the corrected concentrations of both the suppressor and the accelerator can be determined.

Another aspect of the present invention relates to a method for determining concentration(s) of an accelerator and/or a leveler in a sample metal plating solution that contains a suppressor, the accelerator, and the leveler, comprising the steps of:

(a) preparing a plurality of calibration solutions, each of which contains the accelerator and the leveler in different, known concentrations;

(b) measuring electroplating potential that is characteristic of a calibration solution;

(c) calculating concentrations of the accelerator and the leveler in the calibration solution, according to Pulsed Cyclic Galvanostatic Analysis of the measured electroplating potential of the calibration solution;

(d) repeating steps (b) to (c) for each calibration solution, to obtain calculated concentrations of the accelerator and the leveler in each calibration solution;

(e) determining correction coefficients for the accelerator and/or the leveler, based on the known concentrations of the accelerator and/or the leveler and the calculated concentrations of the accelerator and the leveler in the calibration solutions;

(f) measuring electroplating potential that is characteristic of the sample metal plating solution;

(g) calculating concentrations of the accelerator and the leveler in the sample metal plating solution, according to Pulsed Cyclic Galvanostatic Analysis of the measured electroplating potential of the sample metal plating solution; and (h) determining corrected concentration(s) of the accelerator and/or the leveler in the sample metal plating solution, based on the calculated concentrations of the accelerator and the leveler in sample metal plating solution and the correction coefficients determined in step (e) for the accelerator and/or the leveler.

In a preferred embodiment of the present invention, the correction coefficients for both the accelerator and the leveler are determined, so the corrected concentrations of both the accelerator and the leveler can be determined.

A still further aspect of the present invention relates to a method for determining concentration of a target additive in a sample metal plating solution that comprises such target additive and at least one interfering additive. Such method comprises the steps of:

(a) preparing a plurality of calibration solutions, each of which contains the target additive and the interfering additive in different, known concentrations;

(b) measuring electroplating potential that is characteristic of a calibration solution;

(c) calculating concentrations of the target additive and the interfering additive in the calibration solution, according to Pulsed Cyclic Galvanostatic Analysis of the measured electroplating potential of the calibration solution;

(d) repeating steps (b) to (c) for each calibration solution, to obtain calculated concentrations of the target additive and the interfering additive in each calibration solution;

(e) determining correction coefficients for the target additive, based on the known concentrations of the target additive and the calculated concentrations of the target additive and the interfering additive in the calibration solutions;

(f) measuring electroplating potential that is characteristic of the sample metal plating solution;

(g) calculating concentrations of the target additive and the interfering additive in the sample metal plating solution, according to Pulsed Cyclic Galvanostatic Analysis of the measured electroplating potential of the sample metal plating solution; and (h) determining the corrected concentration of the target additive in the sample metal plating solution, based on the calculated concentrations of the target additive and the interfering additive in sample metal plating solution and the correction coefficients determined in step (e) for the target additive.

It is preferred that the corrected concentration of the interfering additive in the sample metal plating solution is also determined, according to the following steps:

(i) determining the correction coefficients for the interfering additive, based on the known concentrations of the interfering additive and the calculated concentrations of the target additive and the interfering additive in the calibration solutions; and (ii) determining the corrected concentration of the interfering additive in the sample metal plating solution, based on the calculated concentrations of the target additive and the interfering additive in said sample metal plating solution and the correction coefficients determined for the interfering target additive in step (i).

Yet another aspect of the present invention relates to an apparatus for determining concentration of a target additive in a sample metal plating solution that comprises said target additive and at least one interfering additive, said apparatus comprises:

(a) a plurality of calibration solutions, each of which contains the target additive and the interfering additive in different, known concentrations;

(b) means for measuring electroplating potentials that is characteristic of each calibration solution;

(c) means for calculating concentrations of the target additive and the interfering additive in each calibration solution, according to Pulsed Cyclic Galvanostatic Analysis of the measured electroplating potential of said calibration solution;

(d) means for determining correction coefficients for the target additive, based on the known concentrations of the target additive and the calculated concentrations of the target additive and the interfering additive in the calibration solutions;

(e) means for measuring electroplating potential that is characteristic of the sample metal plating solution;

(f) means for calculating concentrations of the target additive and the interfering additive in said sample metal plating solution, according to Pulsed Cyclic Galvanostatic Analysis of the measured electroplating potential of said sample metal plating solution; and (g) means for determining the corrected concentration of the target additive in the sample metal plating solution, based on the calculated concentrations of the target additive and the interfering additive in said sample metal plating solution and the correction coefficients determined in step (e) for the target additive.

Additional aspects, features and embodiments of the invention will be more fully apparent from the ensuing disclosure and appended claims.

DETAILED DESCRIPTION OF THE INVENTION, AND PREFERRED EMBODIMENTS THEREOF

Dual-damascene interconnection formation uses sulfuric acid formulated plating baths, which consist of a high concentration of sulfuric acid that functions as the base electrolyte to provide a high electrical conductivity, copper sulfate, and chloride. In addition, several organic additives are employed in such plating baths to control the plating characteristics thereof, such as the mechanical properties of the deposit, distribution of the deposit, and super-conformational or bottom-up fill.

These organic additives are usually present at low concentration in the plating baths, and they are vulnerable to substantial loss during the plating process, due to drag-out and chemical or electrochemical decomposition. While prediction of loss of such organic additives based on coulombs of charge passed and wafers processed can provide criteria for loss estimations, factors such as variable loss rate following an anode change and the build-up of an anode layer make it difficult to accurately predict the loss of such organic additives. Moreover, the analysis of these low concentration organic additives in the presence of the high concentration inorganic bath components presents a considerable analytical challenge.

The PCGA electrochemical techniques provide a simple and sensitive determination of the three most important organic additives contained in a metal plating bath: suppressor, accelerator, and leveler. During a PCGA cycle, a set of current pulses, including a stripping pulse, an equilibration pulse, a nucleation pulse and a metal plating pulse, are applied to a platinum rotating disc electrode (RDE). The electrode potential is monitored during the PCGA cycle.

Figure 1:
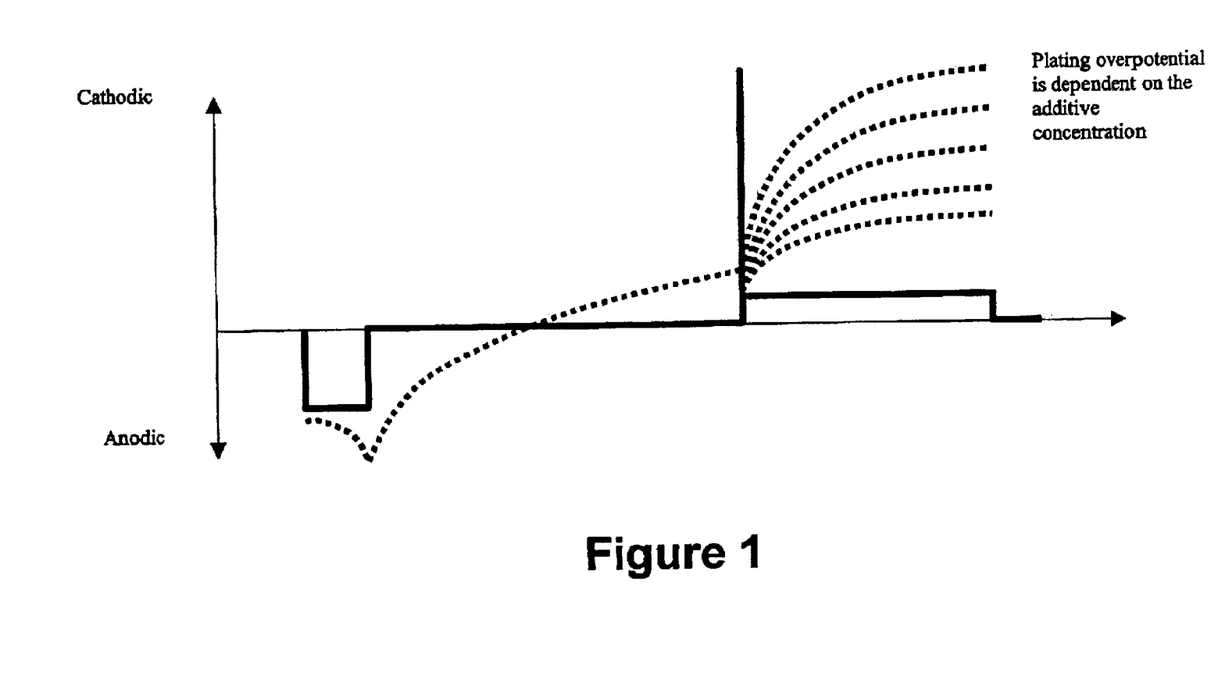
FIG. 1 is a graphic illustration of the current pulse sequence and the electroplating potential that vary with the additive concentration, during the electroplating process.

The metal plating cycle is properly preceded by a nucleation pulse. Application of the nucleation pulse results in a surface state with a high and reproducible concentration of surface nuclei sites (despite variable additive conditions) that allows copper deposition at a fairly low over-potential as well as one that shows lower sensitivity to the suppressor. As the copper grows, a steady state over-potential is reached that shows a strong dependence on the suppressor concentration. FIG. 1 shows a graphic illustration of the current pulse sequence (shown in solid lines), and the corresponding electroplating potentials (shown in dotted line). Note that during the plating period, the dependency of the over-potential on the suppressor concentration increases.

For more details regarding the PCGA method for determining the additive concentration in a metal plating bath, see Robertson U.S. Pat. No. 6,280,602, which was issued to the inventor of the present application on Aug. 28, 2001, and the contents of which are incorporated by reference herein in their entirety for all purposes.

Classification of Additives and Their Electrochemical Characteristics

1. The Suppressor

Typically the suppressor provides a blanket of adsorbed species that increase the polarization over-voltage in a metal plating bath. This has the important effect of changing the primary current density distribution that is geometrically dependent to one that is geometrically independent, i.e., the secondary current distribution. Although the flatness of wafers can guarantee an initially even primary current density distribution, suppressor is necessary to inhibit wild dendritic growth.

Suppressors are typically polyalkene glycol type polymers, which are adsorbed onto the electrode in the presence of chloride to slow down the plating speed.

Figure 2:
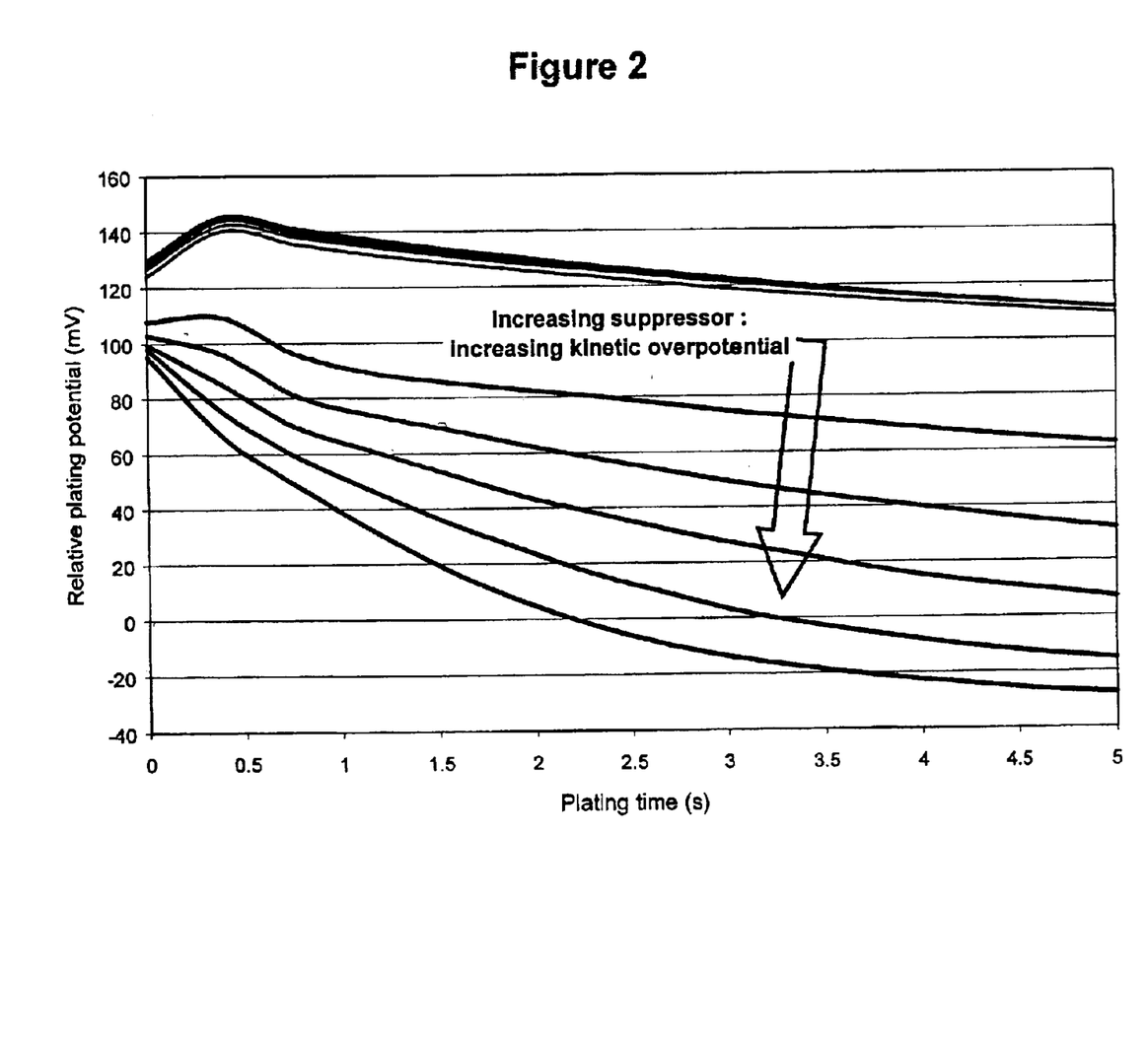
FIG. 2 is a graphic illustration of the effect of suppressor on the electroplating potential.
Figure 4:
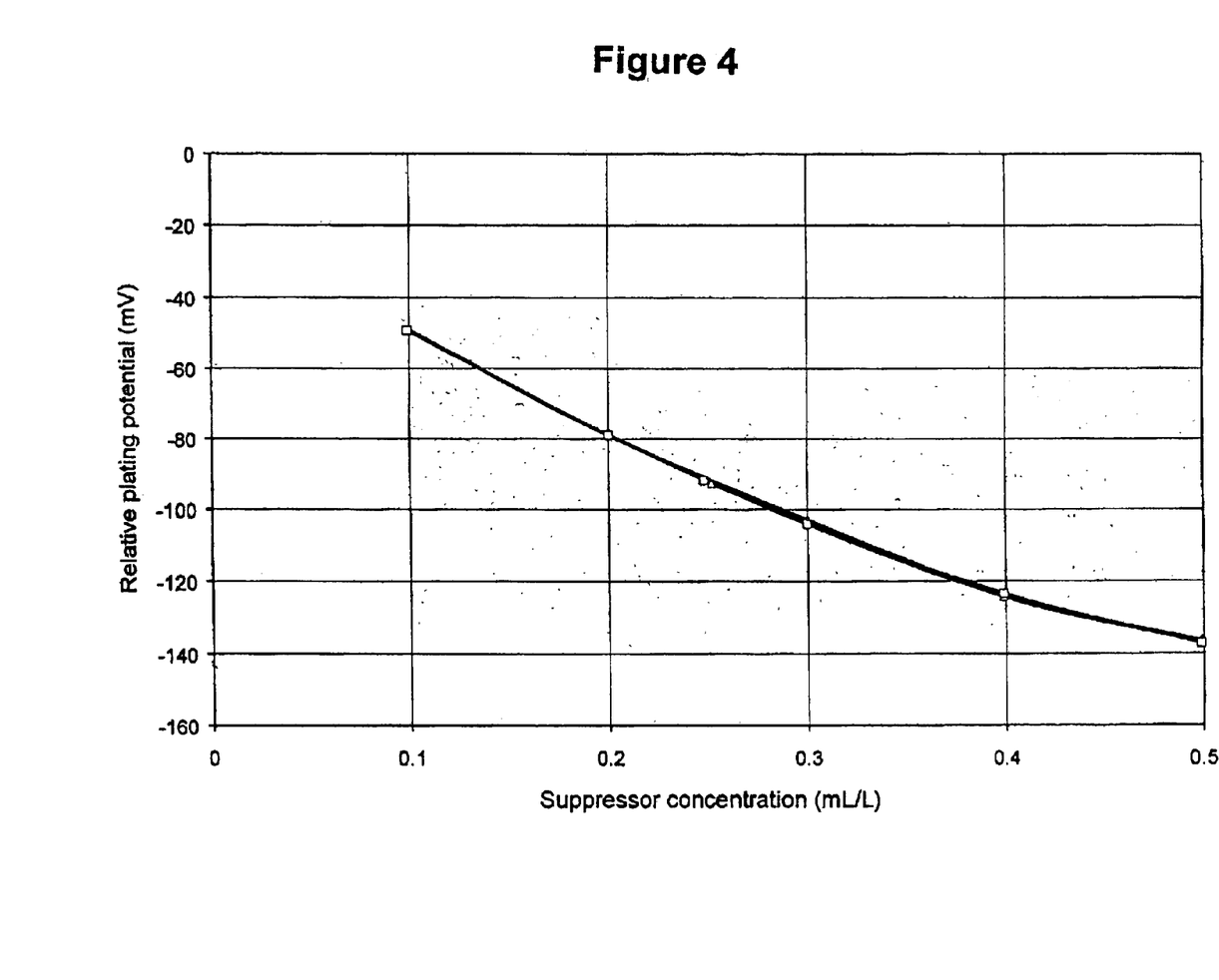
FIG. 4 shows suppressor response curves, which plot the electroplating potential as a function of the suppressor concentration in the metal plating solution.
Figure 5:
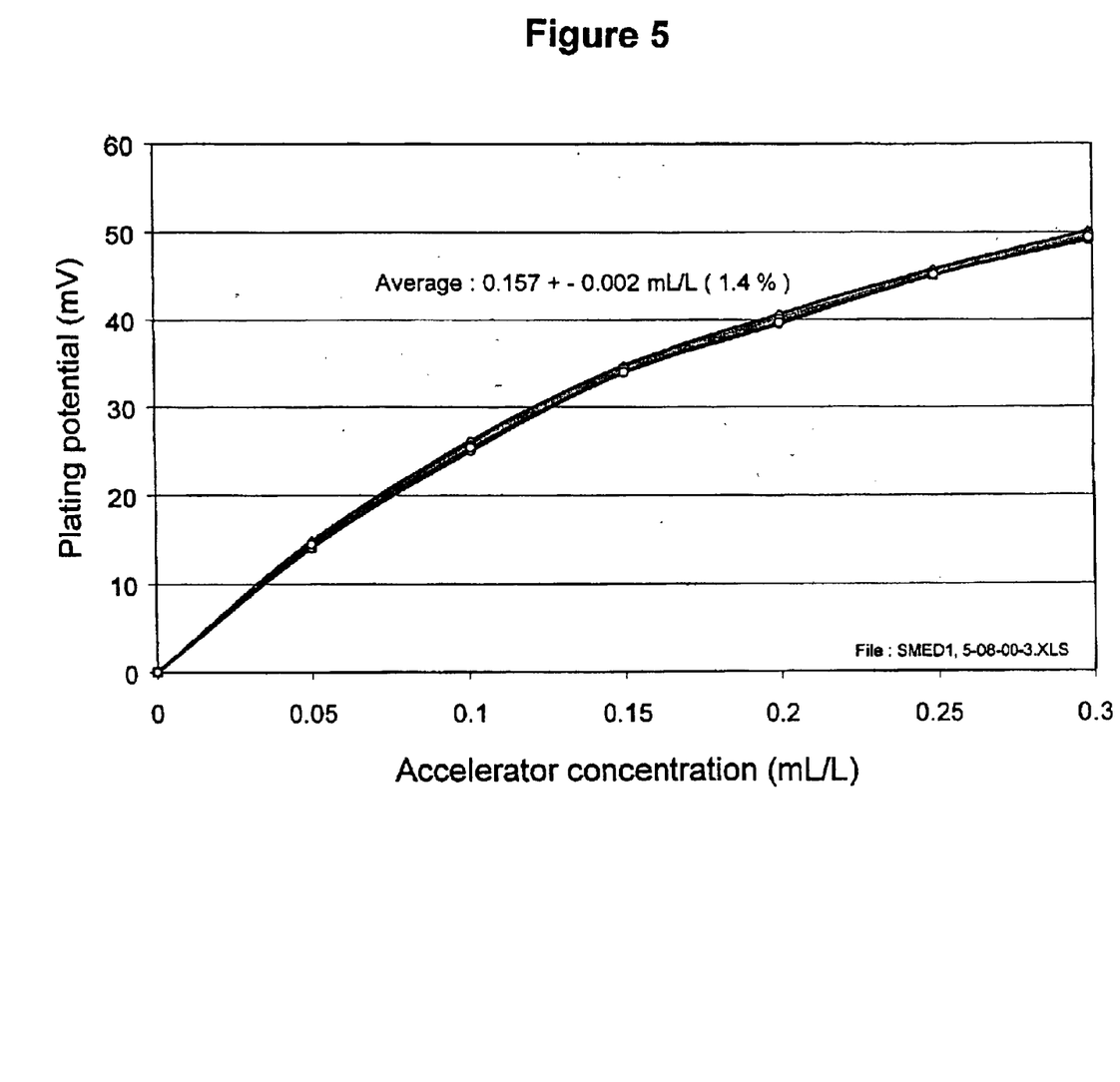
FIG. 5 shows accelerator response curves, which plot the electroplating potential as a function of the accelerator concentration in the metal plating solution.

The PCGA response to the Shipley Ultrafill suppressor is shown in FIG. 2. Here the plating transients go to more cathodic values as suppressor is added, and eventually reach a saturation value where no further plating potential increase is observed. FIG. 4 shows suppressor response curves, by plotting the electroplating potential as a function of the suppressor concentration in the metal plating solution.

2. The Accelerator

Figure 3:
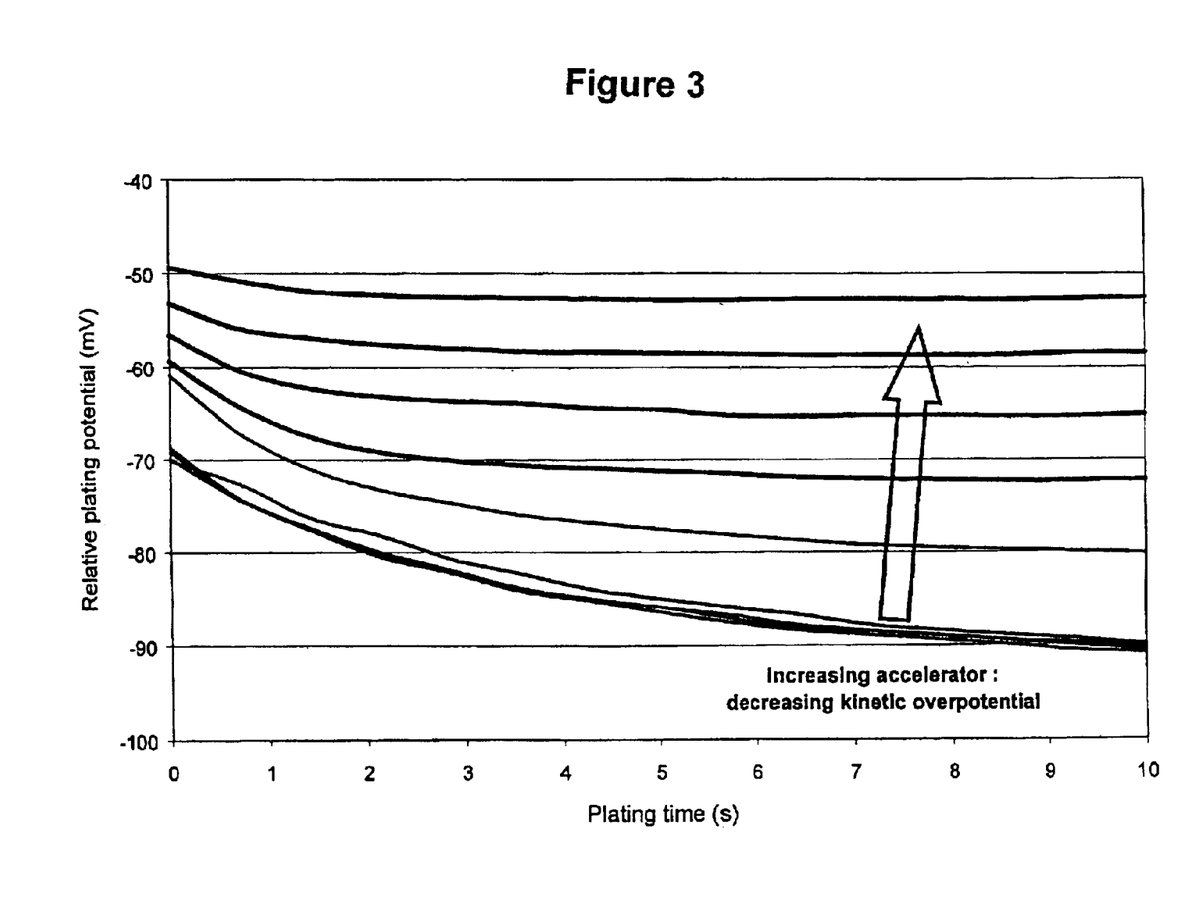
FIG. 3 is a graphic illustration of the effect of accelerator on the electroplating potential.

The accelerator is a compound that in the presence of the suppressor can reduce the over-potential and enhance the plating rate, so as to ease the formation of new growth centers at randomly situated sites. It is a grain refiner/brightener. Moreover, in the context of damascene plating, the accelerator plays the very important role of promoting super-conformal plating. The accelerator is usually a di-(sulfide propane sulfonic acid) type of compound. It has been postulated that it acts as an electron bridge that complexes with the copper ion, and through competitive adsorption, it increases the surface concentration of the copper, thus decreasing the plating over-potential. FIG. 3 is a graphic illustration of the PCGA response to an accelerator, and FIG. 4 shows suppressor response curves, by plotting the electroplating potential as a function of the suppressor concentration in the metal plating solution.

3. The Leveler

The leveler is commonly used in damascene plating, although it is not a requirement for super-conformal plating. It is added to further inhibit growth at defect sites where it is apparently strongly and preferentially adsorbed, in comparison with the accelerator. Its effect is to reduce the suppressor/accelerator interaction, by increasing the plating over-voltage and thus minimizing the plating enhancement provided by the accelerator.

The Two-additive Bath (Suppressor/Accelerator) and Their Interactions

The measurement of accelerator in a two-additive metal plating solution system containing the accelerator and a suppressor is dependent on the concentration of suppressor in the system. Likewise, the measurement of suppressor is dependent on the concentration of accelerator in the system. In order to take this interaction in to account for the concentration measurements of the suppressor and the accelerator, correction equations are designed herein, to establish a set of correction factors for correction of concentrations measurements of both accelerator and suppressor.

The correction equations or models are designed herein by analyzing the interaction between the suppressor and accelerator in the two-additive Enthone Cu bath, using the CuChem® analyzer and software version 5B (manufactured by ATMI, Danbury, Conn.), according to the following experimental protocols:

| | |
|---|---|
| CuChem Analyzer | Software version 5B |
| Chemistry | Enthone |
| Temperature | Ambient |
| Burette 1 | 5 ml/L SC LO (suppressor) |
| Burette 2 | 5 ml/L MD (accelerator) |
| Burette 3 | 5 ml/L SC LO (suppressor) |
| Burette 4 | Enthone VMS |
| Superaccelerator | 250 ml/L MD |
| Supersuppressor | Polyethylene Glycol (PEG) 20,0000 MW 10% solution in water |

5 sample plating solutions are used, which contain: (1) 6 portions of the superaccelerator (MD) and 6 portions of the supersuppressor (LO), (2) 6 portions of the superaccelerator (MD) and 18 portions of the supersuppressor (LO), (3) 18 portions of the superaccelerator (MD) and 18 portions of the supersuppressor (LO), (4) 18 portions of the superaccelerator (MD) and 6 portions of the supersuppressor (LO), and (5) 12 portions of the superaccelerator (MD) and 12 portions of the supersuppressor.

The experimental setup for the CuChem analyzer is shown as follows:

SETUP

SETUP SCREEN #1

Sheet 1

| — | Cl 2 | EMP | FIL 10 00 | — | CCA 2.00 | — | EMP |

Sheet 2

| FIL 10 00 | — | C3 0.5 | BAG | — | CAC 2 | EMP | — |

Sheet 3

| FIL 10 00 | — | EMP | FIL 10 00 | — | CCA 2.00 | EMP | — |

Sheet 4

| S | C 3 0.25 | IN a | EMP | FIL 10.00 | — | — | Cl 1 |

Sheet 5

| EMP | FIL 10 00 | CCA 0.50 | EMP | — | FIL 10.00 | BSP | — |

Sheet 6

| CSP 1 | — | EMP | FIL 10.00 | — | EMP | FIL 10.00 | — |

Sheet 7

| CCA 0.5 | — | EMP | — | — | S | IN s | — |

Sheet 8

| EMP | FIL 10 | — | — | | | | |

SETUP SCREEN #2:

| | | |
|---|---|---|
| Output 1 = | [Acc] | 50 |
| Output 2 = | [Supp] | 50 |
| Output 3 = | [OFF] | 50 |
| Output 4 = | [OFF] | 50 |
| R1 = OFF | 0 | R2 = OFF 0 |
| R3 = OFF | 0 | R4 = OFF 0 |
| R5 = OFF | 0 | R6 = OFF 0 |

SETUP SCREEN #3

| | |
|---|---|
| Calibration Type = | [Process] |
| Calibration factor #1 = | 1 |
| Calibration factor #2 = | 1 |
| Calibration factor #3 = | 1 |
| Analyzer Trigger = | [local] |

SETUP SCREEN #4

| | |
|---|---|
| Analyze frequency = (min.) | 5 |
| Cyclone rinse time = (s) | 10 |
| Temperature Equilibrium Time = (s) | 0 |
| Sample Loop Time = (s) | 9 |
| Cell Empty Time = (min.) | 0.25 |

SETUP SCREEN #5

| | | |
|---|---|---|
| Cleaning | 0 | 0 |
| Equilibrate | 20 | 20 |
| Plate | 18 | 5 |
| Strip | 100 | 100 |
| Nucleate | 5 | 5 |
| | ACC. | SUPP. |

SETUP SCREEN #6

| | | |
|---|---|---|
| # Std. Addns = | 5 | 5 |
| Standard Conc = | 5 | 5 |
| Std. Addn. steps = | 0.08 | 0.1 |
| # Equil. Cycles = | 1 | 1 |
| Equilibrate mode = | Last 1 | Last |
| # E. Cyc. BCK = | 6 | 9 |
| | ACC. | SUPP. |

SETUP SCEEN #7

| | |
|---|---|
| Suppressor transfer volume = (mL) | 1.0 |
| Suppressor loop volume = (mL) | 0.257 |
| Accelerator transfer volume = (mL) | 10 |
| Accelerator loop volume =(mL) | 0.224 |
| Suppressor 2 conc = (mL/L) | 0 |
| Averaging (analysis runs) = | 1 |
| Bad Data point limit = | 15 |

SETUP SCREEN #8

| | |
|---|---|
| Suppressor Offset = | 0 |
| Acccelerator Offset = | 0 |
| Tracking S. Suppressor factor = | 0 |
| Two Point Calibration = | Off |

The sample run order is shown as follows:

| Design 1 | Design 2 | Design 3 |
|---|---|---|
| 18 MD/18 LO | 6 MD/18 LO | 6 MD/6 LO |
| 6 MD/18 LO | 18 MD/18 LO | 18 MD/6 LO |
| 18 MD/6 LO | 6 MD/6 LO | 12 MD/12 LO |
| 6 MD/6 LO | 12 MD/12 LO | 18 MD/6 LO |
| 12 MD/12 LO | 18 MD/6 LO | 6 MD/18 LO |

For the suppressor, each sample solution was measured ten times, and each time, concentration of the suppressor was calculated, according to the PCGA techniques disclosed in Robertson U.S. Pat. No. 6,280,602. The average concentration of the suppressor as result of the ten measurements was recorded, as follows:

TABLE 1

Suppressor (LO) Measurements

| Sample | LO Meas | Std Dev | % RSD |
|---|---|---|---|
| 18 MD/18 LO | 18.22 | 1.45 | 8% |
| 6 MD/18 LO | 18.98 | 0.83 | 4% |
| 18 MD/6 LO | 9.99 | 0.38 | 4% |
| 6 MD/6 LO | 9.40 | 0.41 | 4% |
| 12 MD/12 LO | 14.19 | 1.08 | 8% |

Assuming linearity of the interaction between the accelerator and the suppressor, the following correction equation for the suppressor is established:

$$Supp = f_1(Supp_c, Acc_c)$$

Where Supp is the corrected concentration (i.e., the true concentration) of the suppressor, $Supp_c$ is the calculated concentration (i.e., the measured concentration) of the suppressor, $Acc_c$ is the calculated concentration (i.e., the measured concentration) of the accelerator, and $f_1$ is a suitable mathematical function of the variables $Supp_c$ and $Acc_c$.

One example of the suitable functions $f_1$, according to one embodiment of the present invention, is expressed as the following equation:

$$Supp = X_1 \times Supp_c + X_2 \times Acc_c + X_3 \times Supp_c \times Acc_c + X_4$$

wherein $X_1$, $X_2$, $X_3$, and $X_4$ are the correction coefficients for the suppressor.

By measuring the five sample solutions, five correction equations can be obtained, which contain only four unknown variables $X_1$, $X_2$, $X_3$, and $X_4$. Therefore, the values of the correction coefficients $X_1$, $X_2$, $X_3$, and $X_4$ for the suppressor measurement can be readily calculated, as follows:

$X_1 = 1.087143$
$X_2 = -0.28575$
$X_3 = 0.022498$
$X_4 = -3.57195$

When a new sample solution with unknown suppressor concentration is provided, one can measure the suppressor and the accelerator concentrations in such sample solution, according to the PCGA techniques disclosed in Robertson U.S. Pat. No. 6,280,602. The correction equation and the correction coefficient calculated hereinabove can then be used to determine the corrected concentration (i.e., the true concentration) of the suppressor in the sample solution.

Figure 6:
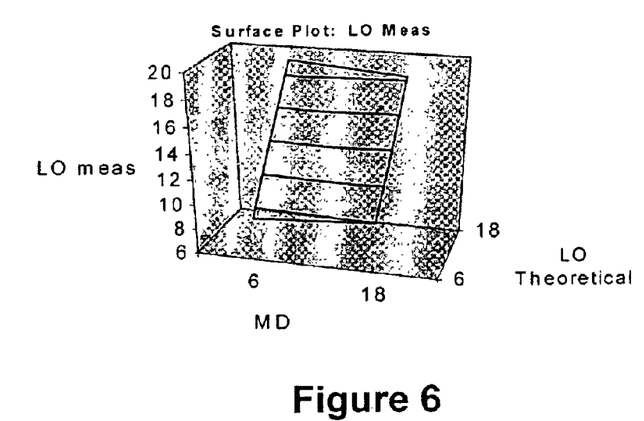
FIG. 6 is a suppressor correction graph, which compares the corrected suppressor concentrations determined according to the present invention, with the calculated suppressor concentrations according to the conventional PCGA method, in metal plating solutions that comprises the suppressor and the accelerator.

The correction results are best illustrated by a suppressor correction graph in FIG. 6, which compares the corrected suppressor (LO) concentrations determined according to the present invention, with the calculated suppressor (LO) concentrations according to the conventional PCGA method, depending on the accelerator (MD) concentrations in the sample solutions.

For the accelerator, each sample solution was also measured ten times, and each time, concentration of the accelerator was calculated, according to the PCGA techniques disclosed in Robertson U.S. Pat. No. 6,280,602. The average concentration of the accelerator as result of the ten measurements was recorded, as follows:

| Sample | MD meas | Std Dev | % RSD |
|---|---|---|---|
| Design 1 | | | |
| 18 MD/18 LO | 14.74 | 0.36 | 2% |
| 6 MD/18 LO | 6.70 | 0.26 | 4% |
| 18 MD/6 LO | 21.66 | 0.97 | 4% |
| 6 MD/6 LO | 8.53 | 0.29 | 3% |
| 12 MD/12 LO | 12.00 | 0.35 | 3% |
| Design 2 | | | |
| 18 MD/18 LO | 13.51 | 0.4 | 3% |
| 6 MD/18 LO | 6.73 | 0.24 | 4% |
| 18 MD/6 LO | 21.31 | 1.88 | 9% |
| 6 MD/6 LO | 8.70 | 0.34 | 4% |
| 12 MD/12 LO | 11.90 | 0.41 | 3% |
| Design 3 | | | |
| 18 MD/18 LO | 14.31 | 0.72 | 5% |
| 6 MD/18 LO | 6.41 | 0.16 | 2% |
| 18 MD/6 LO | 19.77 | 0.57 | 3% |
| 6 MD/6 LO | 8.98 | 0.58 | 6% |
| 12 MD/12 LO | 11.60 | 0.33 | 3% |

The calculated concentrations of the accelerator were then compared to the known concentrations of the accelerator in the sample solutions from each design, as follows:

| Sample | Design 1 MD Meas | Design 2 MD Meas | Design 3 MD Meas | avg | Std Dev | % RSD |
|---|---|---|---|---|---|---|
| 18 MD/18 LO | 14.74 | 13.51 | 14.31 | 14.19 | 0.62 | 4% |
| 6 MD/18 LO | 6.70 | 6.73 | 6.40 | 6.61 | 0.18 | 3% |
| 12 MD/12 LO | 12.00 | 11.90 | 11.60 | 11.83 | 0.21 | 2% |
| 6 MD/6 LO | 8.53 | 8.70 | 8.98 | 8.74 | 0.23 | 3% |
| 18 MD/6 LO | 21.66 | 21.31 | 19.76 | 20.91 | 1.01 | 5% |

It is clear from the above measurement data that the concentration of suppressor (LO) in the sample solutions affects the accelerator (MD) concentration measurements.

Therefore, the following correction equation for the accelerator concentration measurements can be established:

$$Acc = f_2(Supp_c, Acc_c)$$

Where Acc is the corrected concentration of the accelerator, $Supp_c$ is the calculated concentration (i.e., the measured concentration) of the suppressor, $Acc_c$ is the calculated concentration (i.e., the measured concentration) of the accelerator, and $f_2$ is a suitable mathematical function of the variables $Spp_c$ and $Acc_c$.

One example of the suitable function $f_2$, according to one embodiment of the present invention, is expressed as the following equation:

$$Acc = X_a \times Acc_c + X_b \times Supp_c \times Supp_c + X_c \times Acc_c + X_d$$

wherein $X_a$, $X_b$, $X_c$, and $X_d$ are the correction coefficients for the accelerator.

By measuring the five sample solutions, five correction equations can be obtained, which contain only four unknown variables $X_a$, $X_b$, $X_c$, and $X_d$. Therefore, the values of the correction coefficients $X_a$, $X_b$, $X_c$, and $X_d$ for the accelerator measurement can be readily calculated, as follows:

$X_a = 0.195013$
$X_b = -0.30756$
$X_c = 0.07742$
$X_d = 0.835735$

When a new sample solution with unknown accelerator concentration is provided, one can measure the suppressor and the accelerator concentrations in such sample solution, according to the PCGA techniques disclosed in Robertson U.S. Pat. No. 6,280,602. The correction equation and the correction coefficient calculated hereinabove can then be used to determine the corrected concentration (i.e., the true concentration) of the accelerator in the sample solution.

Figure 7:
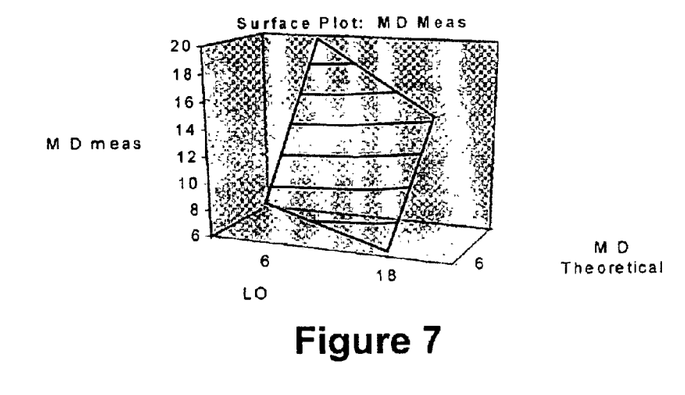
FIG. 7 is an accelerator correction graph, which compares the corrected accelerator concentrations determined according to the present invention, with the calculated accelerator concentrations according to the prior art PCGA method, in metal plating solutions that comprises the suppressor and the accelerator.

The accelerator correction results are best illustrated by an accelerator correction graph in FIG. 7, which compares the corrected accelerator (MD) concentrations determined according to the present invention, with the calculated accelerator (MD) concentrations according to the conventional PCGA method, depending on the suppressor (LO) concentrations in the sample solutions.

Note that the same set of sample solutions and corresponding measurements thereof can also be used to concurrently determine the correction coefficients of both the suppressor and the accelerator, so that the corrected concentrations of the suppressor and the accelerator in a sample solution of unknown LO/MD concentration can be calculated based on one set of experimental data.

The Three Additive Bath (Suppressor/Accelrator/Leveler) and Their Interactions

The measurement of accelerator in a three-additive metal plating solution system containing the suppressor, the accelerator, and the leveler (such as the Enthone Cubath Viaform ECD bath) is dependent on the concentration of leveler in the system.

Figure 8:
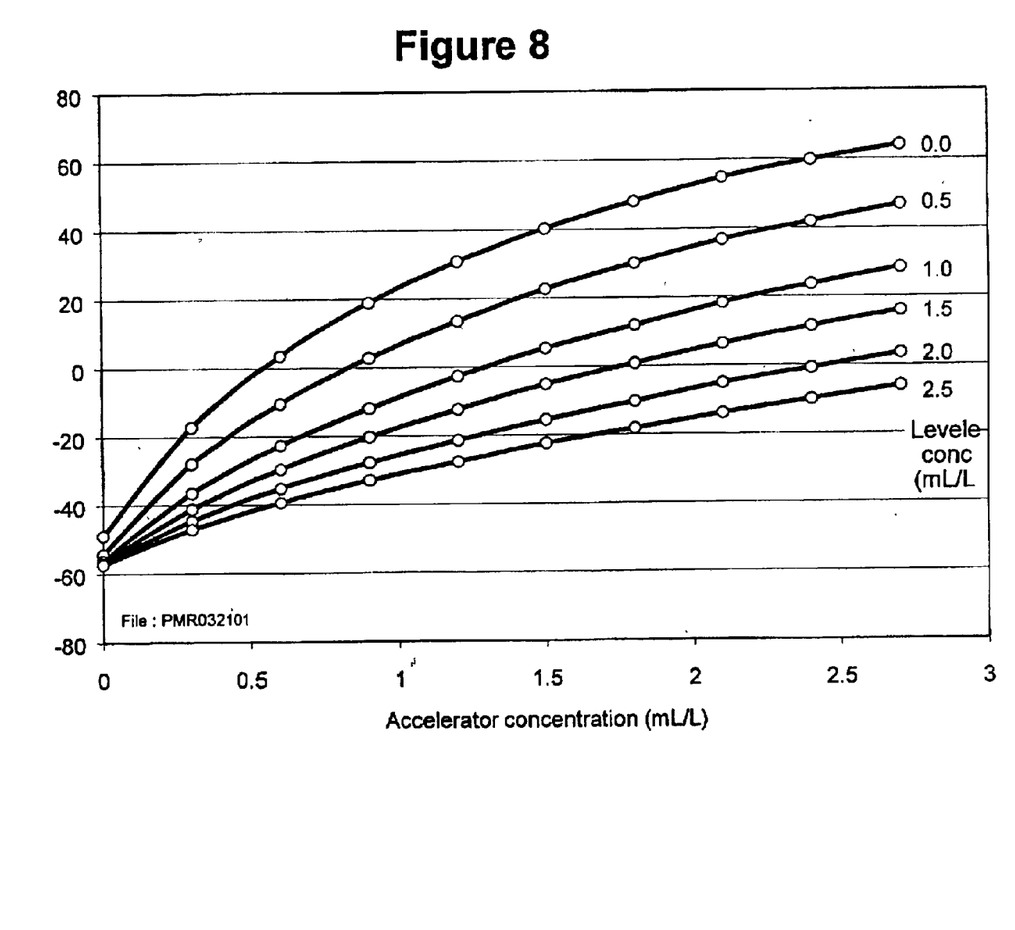
FIG. 8 is a graphic illustration of the effect of varying leveler concentration upon the accelerator response measured in a metal plating solution.

In the presence of the leveler, the accelerator response is reduced, due to the interacting effects of the leveler with that of the accelerator. FIG. 8 is a graph showing a graphic illustration of the effect of varying leveler concentration upon the accelerator response, as measured in a three-additive metal plating solution. Under nominal bath compositions, the leveler interaction can reduce the accelerator response by as much as 50%.

Figure 9:
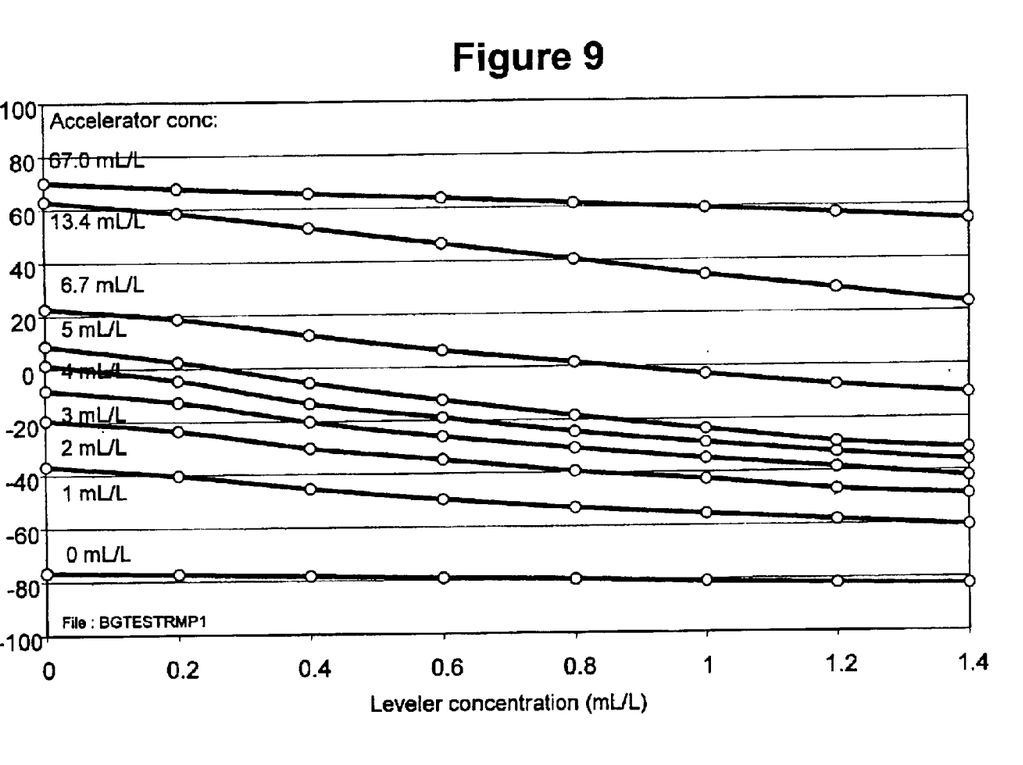
FIG. 9 is a graphic illustration of the effect of varying accelerator concentration upon a leveler response measured in a metal plating solution.

Likewise, the measurement of leveler in the three-additive metal plating solution is dependent on the concentration of accelerator therein. The leveler response is increased in plating solutions where the concentration of accelerator is higher. FIG. 9 is a graphic illustration of the effect of varying accelerator concentration upon leveler response, as measured in a three-additive metal plating solution.

Figure 10:
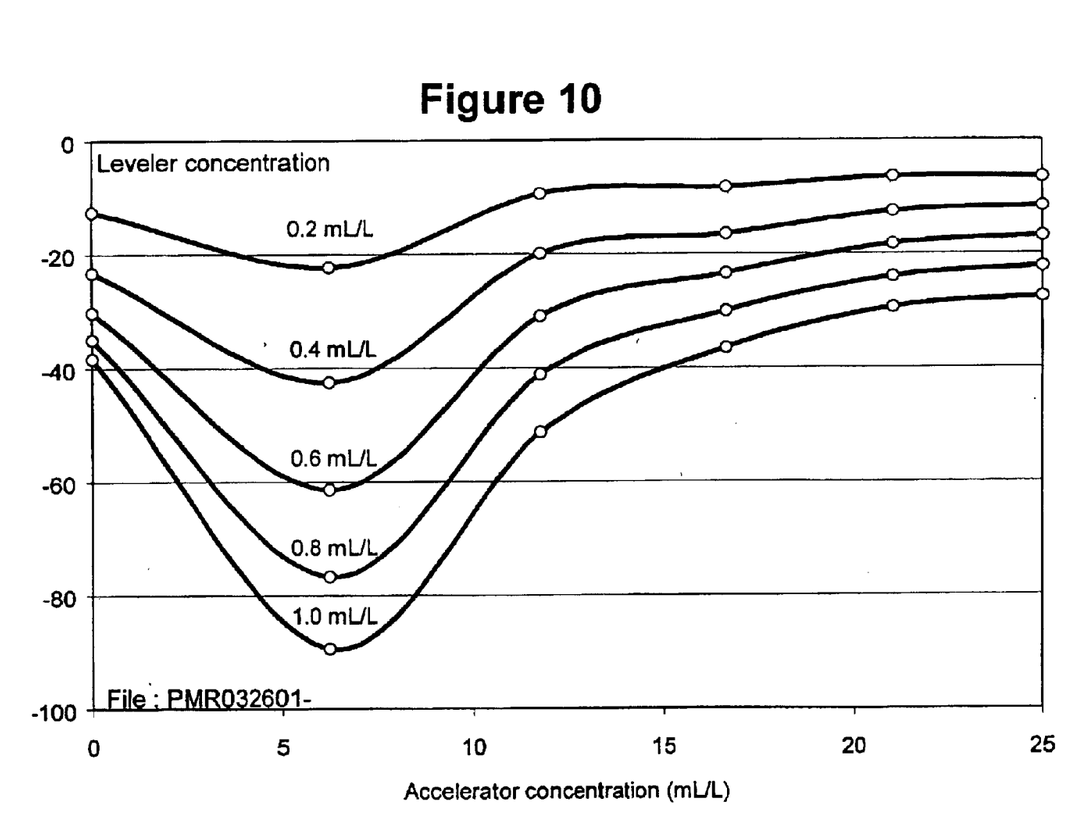
FIG. 10 is a graph showing the existence of an optimal accelerator concentration, at which the leveler shows the maximum interfering effect.

The interference of the leveler on the accelerator/suppressor interaction forms the basis of the leveler determination. In principle conditions are set up with excess suppressor (PEG type) and accelerator, so that the accelerator causes a well-defined lowering of the over-potential. Due to the competitive nature of the adsorption of the three additives, there exists an optimal concentration of accelerator that demonstrates maximum leveler interference, as shown in FIG. 10. At accelerator concentrations lower than the optimal concentration, the accelerator enhancement and the corresponding interaction with the leveler is small, whereas at accelerator concentrations higher than the optimal concentration, there is a very strong adsorption of accelerator, which low leveler concentrations have little impact on. Therefore, by suitably conditioning the accelerator and suppressor concentrations in the metal plating bath, one can achieve a leveler response of over 100 mV.

In order to take the interaction between the accelerator and the leveler into account for the concentration measurements of the accelerator and the leveler, correction equations are designed herein, to establish a set of correction coefficients, for correction of concentrations measurements of the accelerator and the leveler.

Due to the mutual interactions between the accelerator and the leveler, a mathematical modeling of the plating over-potential data, as obtained from calibration of multiple sample solutions, provides the most reliable method for eliminating the cross-interactions between accelerator and leveler.

Specifically, for the accelerator concentration measurement, the following correction equation is provided:

$$Acc = f_3(Lev_c, Acc_c)$$

Where Acc is the corrected concentration of the accelerator, $Acc_c$ is the calculated concentration (i.e., the measured concentration) of the accelerator, $Lev_c$ is the calculated concentration (i.e., the measured concentration) of the leveler, and $f_3$ is a suitable mathematical function of the variables $Supp_c$ and $Acc_c$.

One example of the suitable function $f_3$, according to one embodiment of the present invention, is expressed as the following equation:

$$Acc = Y_1 + Acc_c \times (Y_2 + Y_3 \times Lev_c + Y_4 \times Lev_c \times Lev_c)$$

wherein $Y_1, Y_2, Y_3$, and $Y_4$ are the correction coefficients for the accelerator.

For the leveler concentration measurement, the following correction equation is provided:

$$Lev = f_4(Lev_c, Acc_c)$$

Where Lev is the corrected concentration of the leveler, $Lev_c$ is the calculated concentration (i.e., the measured concentration) of the leveler, $Acc_c$ is the calculated concentration (i.e., the measured concentration) of the accelerator, and $f_4$ is a suitable mathematical function of the variables $Lev_c$ and $Acc_c$.

One example of the suitable function $f_4$, according to one embodiment of the present invention, is expressed as the following equation:

$$Lev = Y_a + Lev_c \times (Y_b + Y_c \times Acc_c + Y_d \times Acc_c)$$

wherein $Y_a, Y_b, Y_c$, and $Y_d$ are the correction coefficients for the leveler.

By determining the correction coefficients as described hereinabove for the accelerator or the leveler, one can readily correct the concentration measurements of the accelerator or the leveler obtained according to the conventional PCGA method. For a new chemistry, it is only necessary to run a matrix of about 8 calibration solutions to provide an exact description of the matrix effect. The PCGA method itself is self-calibrating and provides stable raw data that can be processed by the matrix correction algorithm.

The accelerator correction coefficients $Y_1, Y_2, Y_3$, and $Y_4$ and the leveler correction coefficients $Y_a, Y_b, Y_c$, and $Y_d$ can be concurrently determined, using the same set of calibration solution and corresponding measurements thereof, so as to concurrently determine the corrected concentration of both the accelerator and the leveler in a new chemistry of unknown accelerator and leveler concentrations.

Figure 11:
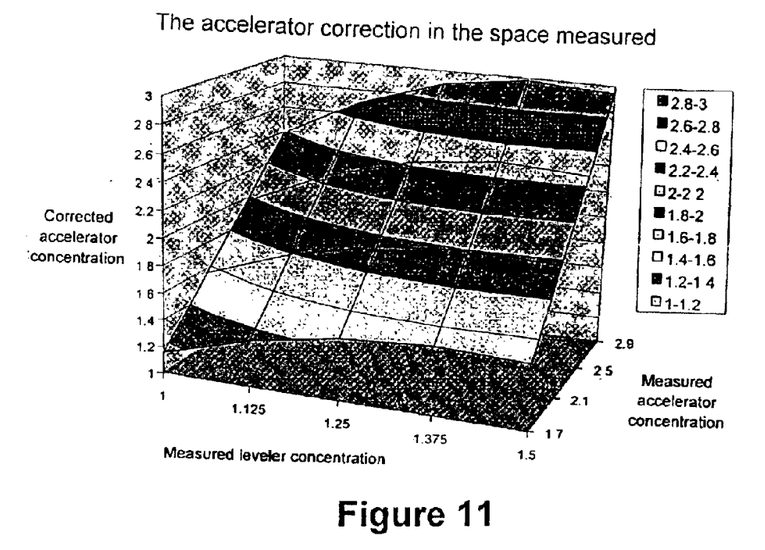
FIG. 11 is an accelerator correction graph, which compares the corrected accelerator concentrations determined according to the present invention, with the calculated accelerator concentrations according to the prior art PCGA method, in metal plating solutions that comprises the suppressor, the accelerator, and the leveler.
Figure 12:
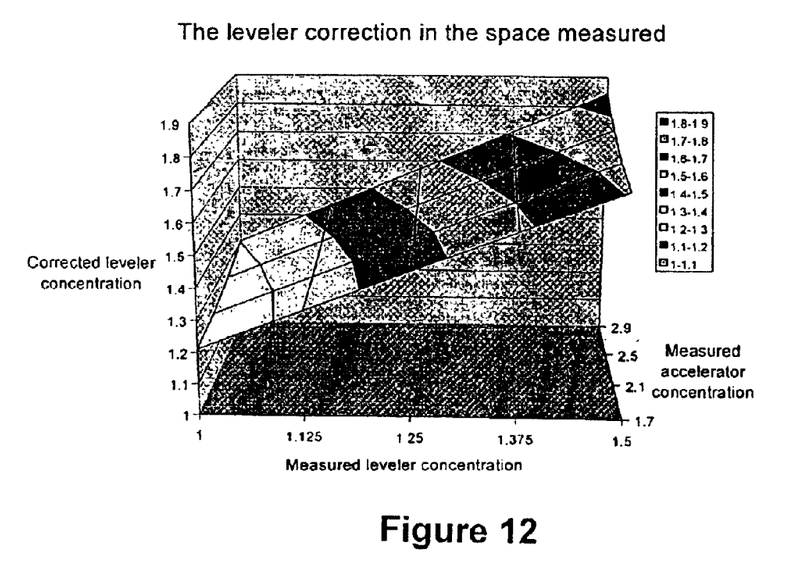
FIG. 12 is a leveler correction graph, which compares the corrected leveler concentrations determined according to the present invention, with the calculated leveler concentrations according to the prior art PCGA method, in metal plating solutions that comprises the suppressor, the accelerator, and the leveler.

FIG. 11 shows an accelerator correction graph, which compares the corrected accelerator concentrations determined according to the present invention, with the calculated accelerator concentrations according to the prior art PCGA method, in metal plating solutions that comprises the suppressor, the accelerator, and the leveler. FIG. 12 shows a leveler correction graph, which compares the corrected leveler concentrations determined according to the present invention, with the calculated leveler concentrations according to the prior art PCGA method, in metal plating solutions that comprises the suppressor, the accelerator, and the leveler.

The present invention therefore utilizes mathematical correction model in combination with the conventional PCGA chrono-potentiometric analysis method, to eliminate the interaction between the observed electrochemical behavior of suppressor, accelerator, and leveler, therefore allowing accurate determination of the concentration of these critical bath components.

The method as described hereinabove can be readily extrapolated to determine the concentration of a target additive in a metal plating solution that contains both the target additive and at least one interfering additive that interferes with the electro-potential response of such target additive. If such target additive and the interfering additive are mutually interfering, the concentration measurements of either can be corrected by taking into account of the concentration of the other, according to the above-described method.

Although the invention has been variously disclosed herein with reference to illustrative embodiments and features, it will be appreciated that the embodiments and features described hereinabove are not intended to limit the scope of the invention, and that other variations, modifications and other embodiments will suggest themselves to those of ordinary skill in the art. The invention therefore is to be broadly construed, consistent with the claims hereafter set forth.

What is claimed is:

1. A method for determining concentration(s) of a suppressor and/or an accelerator in a sample metal plating solution that contains both the suppressor and the accelerator, said method comprising the steps of:
    (a) preparing a plurality of calibration solutions, each of which contains the suppressor and the accelerator in different, known concentrations;
    (b) measuring electroplating potential that is characteristic of a calibration solution;
    (c) calculating concentrations of the suppressor and the accelerator in said calibration solution, according to Pulsed Cyclic Galvanostatic Analysis of the measured electroplating potential of said calibration solution;
    (d) repeating steps (b) to (c) for each calibration solution, to obtain calculated concentrations of the suppressor and the accelerator in each calibration solution;
    (e) determining correction coefficients for the suppressor and/or the accelerator, based on the known concentrations of the suppressor and/or the accelerator and the calculated concentrations of the suppressor and the accelerator in the calibration solutions;
    (f) measuring electroplating potential that is characteristic of the sample metal plating solution;
    (g) calculating concentrations of the suppressor and the accelerator in said sample metal plating solution, according to Pulsed Cyclic Galvanostatic Analysis of the measured electroplating potential of said sample metal plating solution; and
    (h) determining corrected concentration(s) of the suppressor and/or the accelerator in the sample metal plating solution, based on the calculated concentrations of the suppressor and the accelerator in said sample metal plating solution and the correction coefficients determined in step (e) for the suppressor and/or the accelerator.

2. The method of claim 1, wherein the corrected concentration of the suppressor is determined according to the following equation:

$$Supp = f_1(Supp_c, Acc_c)$$

Where Supp is the corrected concentration of the suppressor, $Supp_c$ is the calculated concentration of the suppressor, $Acc_c$ is the calculated concentration of the accelerator, and $f_1$ is a mathematical function.

3. The method of claim 2, wherein the functions is expressed by the following equation:

$$Supp = X_1 \times Supp_c + X_2 \times Acc_c \times X_3 \times Supp_c \times Acc_c \times X_4$$

wherein $X_1$, $X_2$, $X_3$, and $X_4$ are the correction coefficients for the suppressor.

4. The method of claim 2, wherein a sufficient number of calibration solutions that contain the suppressor and the accelerator in different, known concentrations are prepared to allow mathematical solution of the functions $f_1$.

5. The method of claim 3, wherein five calibration solutions that contain the suppressor and the accelerator in different, known concentrations are prepared and measured.

6. The method of claim 1, wherein the corrected concentration of the accelerator is determined according to the following equation:

$$Acc = f_2(Supp_c, Acc_c)$$

Where Acc is the corrected concentration of the accelerator, $Supp_c$ is the calculated concentration of the suppressor, $Acc_c$ is the calculated concentration of the accelerator, and $f_2$ is a mathematical function.

7. The method of claim 6, wherein the function $f_2$ is expressed by the following equation:

$$Acc = X_a \times Acc_c + X_b \times Supp_c + X_c \times Acc_c \times Supp_c + X_d$$

wherein $X_a$, $X_b$, $X_c$, and $X_d$ are the correction coefficients for the accelerator.

8. The method of claim 6, wherein a sufficient number of calibration solutions that contain the suppressor and the accelerator in different, known concentrations are prepared to allow mathematical solution of the function $f_2$.

9. The method of claim 7, wherein five calibration solutions that contain the suppressor and the accelerator in different, known concentrations are prepared and measured.

10. The method of claim 1, wherein the correction coefficients for both the suppressor and the accelerator are determined in step (e), so as to determine the corrected concentrations of both the suppressor and the accelerator in step (h).

11. The method of claim 10, wherein five calibration solutions that contained the suppressor and the accelerator in different, known concentrations are prepared and measured.

12. A method for determining concentration(s) of an accelerator and/or a leveler in a sample metal plating solution that contains a suppressor, the accelerator, and the leveler, said method comprising the steps of:
    (a) preparing a plurality of calibration solutions, each of which contains the accelerator and the leveler in different, known concentrations;
    (b) measuring electroplating potential that is characteristic of a calibration solution;
    (c) calculating concentrations of the accelerator and the leveler in said calibration solution, according to Pulsed Cyclic Galvanostatic Analysis of the measured electroplating potential of said calibration solution;
    (d) repeating steps (b) to (c) for each calibration solution, to obtain calculated concentrations of the accelerator and the leveler in each calibration solution;
    (e) determining correction coefficients for the accelerator and/or the leveler, based on the known concentrations of the accelerator and/or the leveler and the calculated concentrations of the accelerator and the leveler in the calibration solutions;

(f) measuring electroplating potential that is characteristic of the sample metal plating solution;

(g) calculating concentrations of the accelerator and the leveler in said sample metal plating solution, according to Pulsed Cyclic Galvanostatic Analysis of the measured electroplating potential of said sample metal plating solution; and (h) determining corrected concentration(s) of the accelerator and/or the leveler in the sample metal plating solution, based on the calculated concentrations of the accelerator and the leveler in said sample metal plating solution and the correction coefficients determined in step (e) for the accelerator and/or the leveler.

13. The method of claim 12, wherein the corrected concentration of the accelerator is determined according to the following equation:

$$Acc=f_3(Lev_c, Acc_c)$$

Where Acc is the corrected concentration of the accelerator, $Acc_c$ is the calculated concentration of the accelerator, $Lev_c$ is the calculated concentration of the leveler, and $f_3$ is a mathematical function.

14. The method of claim 13, wherein of the functions is expressed by the following equation:

$$Acc=Y_1+Acc_c \times (Y_2+Y_3 \times Lev_c+Y_4 \times Lev_c \times Lev_c)$$

wherein $Y_1, Y_2, Y_3$, and $Y_4$ are the correction coefficients for the accelerator.

15. The method of claim 12, wherein the corrected concentration of the leveler is determined according to the following equation:

$$Lev=f_4(Lev_c, Acc_c)$$

Where Lev is the corrected concentration of the leveler, $Lev_c$ is the calculated concentration of the leveler, $Acc_c$ is the calculated concentration of the accelerator, and $f_4$ is a mathematical function.

16. The method of claim 15, wherein the functions is expressed by the following equation:

$$Lev=Y_a+Lev_c \times (Y_b \times Y_c \times Acc_c+Y_d \times Acc_c \times Acc_c)$$

wherein $Y_a, Y_b, Y_c$, and $Y_d$ are the correction coefficients for the leveler.

17. The method of claim 12, wherein the correction coefficients for both the accelerator and the leveler are determined in step (e), so as to determine the corrected concentrations of both the accelerator and the leveler in step (h).

18. A method for determining concentration of a target additive in a sample metal plating solution that comprises said target additive and at least one interfering additive, said method comprising the steps of:

(a) preparing a plurality of calibration solutions, each of which contains the target additive and the interfering additive in different, known concentrations;

(b) measuring electroplating potential that is characteristic of a calibration solution;

(c) calculating concentrations of the target additive and the interfering additive in said calibration solution, according to Pulsed Cyclic Galvanostatic Analysis of the measured electroplating potential of said calibration solution;

(d) repeating steps (b) to (c) for each calibration solution, to obtain calculated concentrations of the target additive and the interfering additive in each calibration solution;

(e) determining correction coefficients for the target additive, based on the known concentrations of the target additive and the calculated concentrations of the target additive and the interfering additive in the calibration solutions;

(f) measuring electroplating potential that is characteristic of the sample metal plating solution;

(g) calculating concentrations of the target additive and the interfering additive in said sample metal plating solution, according to Pulsed Cyclic Galvanostatic Analysis of the measured electroplating potential of said sample metal plating solution; and (h) determining the corrected concentration of the target additive in the sample metal plating solution, based on the calculated concentrations of the target additive and the interfering additive in said sample metal plating solution and the correction coefficients determined in step (e) for the target additive.

19. The method of claim 18, further comprising the steps of:

(i) determining the correction coefficients for the interfering additive, based on the known concentrations of the interfering additive and the calculated concentrations of the target additive and the interfering additive in the calibration solutions; and (j) determining the corrected concentration of the interfering additive in the sample metal plating solution, based on the calculated concentrations of the target additive and the interfering additive in said sample metal plating solution and the correction coefficients determined for the interfering target additive in step (i).

20. An apparatus for determining concentration of a target additive in a sample metal plating solution that comprises said target additive and at least one interfering additive, said apparatus comprises:

(a) a plurality of calibration solutions, each of which contains the target additive and the interfering additive in different, known concentrations;

(b) means for measuring electroplating potentials that is characteristic of each calibration solution;

(c) means for calculating concentrations of the target additive and the interfering additive in each calibration solution, according to Pulsed Cyclic Galvanostatic Analysis of the measured electroplating potential of said calibration solution;

(d) means for determining correction coefficients for the target additive, based on the known concentrations of the target additive and the calculated concentrations of the target additive and the interfering additive in the calibration solutions;

(e) means for measuring electroplating potential that is characteristic of the sample metal plating solution;

(f) means for calculating concentrations of the target additive and the interfering additive in said sample metal plating solution, according to Pulsed Cyclic Galvanostatic Analysis of the measured electroplating potential of said sample metal plating solution; and (g) means for determining the corrected concentration of the target additive in the sample metal plating solution, based on the calculated concentrations of the target additive and the interfering additive in said sample metal plating solution and the correction coefficients determined in step (e) for the target additive.

21. The apparatus of claim 20, further comprises:

(i) means for determining the correction coefficients for the interfering additive, based on the known concentrations of the interfering additive and the calculated concentrations of the target additive and the interfering additive in the calibration solutions; and (j) means for determining the corrected concentration of the interfering additive in the sample metal plating solution, based on the calculated concentrations of the target additive and the interfering additive in said sample metal plating solution and the correction coefficients determined for the interfering target additive in step (i).

22. The apparatus of claim 20, wherein the target additive comprises suppressor, wherein the interfering additive comprises accelerator.

23. The apparatus of claim 20, wherein the target additive comprises accelerator, wherein the interfering additive comprises leveler, and wherein the sample metal plating solution comprises a suppressor, the accelerator, and the leveler.

* * * * *